United States Patent
Park et al.

(10) Patent No.: US 9,220,481 B2
(45) Date of Patent: Dec. 29, 2015

(54) DIAGNOSTIC IMAGE GENERATING APPARATUS, MEDICAL IMAGE SYSTEM, AND BEAMFORMING METHOD

(75) Inventors: Sung-chan Park, Suwon-si (KR);
Kyu-hong Kim, Seongnam-si (KR);
Jung-ho Kim, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/487,566

(22) Filed: Jun. 4, 2012

(65) Prior Publication Data
US 2013/0090559 A1    Apr. 11, 2013

(30) Foreign Application Priority Data
Oct. 5, 2011    (KR) .................. 10-2011-0101490

(51) Int. Cl.
*A61B 8/14*        (2006.01)
*A61B 8/08*        (2006.01)
*G01S 15/89*       (2006.01)

(52) U.S. Cl.
CPC .............. *A61B 8/5207* (2013.01); *A61B 8/5269* (2013.01); *G01S 15/8959* (2013.01); *G01S 15/8977* (2013.01); *A61B 8/14* (2013.01)

(58) Field of Classification Search
CPC ...... A61B 8/14; A61B 8/5207; A61B 8/5269; G01S 15/8959; G01S 15/8977
See application file for complete search history.

(56) References Cited

U.S. PATENT DOCUMENTS

| | | | |
|---|---|---|---|
| 6,491,631 B2 | 12/2002 | Chiao et al. | |
| 2007/0239002 A1 | 10/2007 | Alam | |
| 2008/0253675 A1* | 10/2008 | Chou et al. | 382/255 |
| 2010/0185093 A1* | 7/2010 | Hamilton | 600/443 |
| 2010/0240992 A1 | 9/2010 | Hao | |

FOREIGN PATENT DOCUMENTS

| | | |
|---|---|---|
| JP | 2009-247511 A | 10/2009 |
| JP | 2010-63829 A | 3/2010 |

OTHER PUBLICATIONS

Michailovich, Oleg et al., "Blind deconvolution of medical ultrasound images: A parametric inverse filtering approach," *IEEE Transactions on Image Processing*, vol. 16 No. 12 (Dec. 2007): pp. 3005-3019.

* cited by examiner

*Primary Examiner* — Mark Remaly
(74) *Attorney, Agent, or Firm* — NSIP Law

(57) ABSTRACT

A diagnostic image generating apparatus, a medical image system, and a beamforming method are provided. The diagnostic image generating apparatus includes a transmitting unit configured to transmit a modulated transmission signal to a subject, a reception beamforming unit configured to form a reception beam by beamforming echo signals reflected from the subject, a point spread function (PSF) estimating unit configured to estimate a PSF for each region according to the formed reception beam, a filtering unit configured to filter the formed reception beam according to the estimated PSF, and a diagnostic image generating unit configured to generate a diagnostic image according to the filtered reception beam.

7 Claims, 4 Drawing Sheets

DIAGNOSTIC IMAGE GENERATING APPARATUS, MEDICAL IMAGE SYSTEM, AND BEAMFORMING METHOD

CROSS-REFERENCE TO RELATED APPLICATIONS

This application claims the benefit under 35 U.S.C. §119(a) of Korean Patent Application No. 10-2011-0101490, filed on Oct. 5, 2011, in the Korean Intellectual Property Office, the entire disclosure of which is incorporated herein by reference for all purposes.

BACKGROUND

1. Field

The following description relates to a diagnostic image generating apparatus, a medical image system, and a beamforming method.

2. Description of Related Art

In ultrasonic image processing, a function defining a lateral shape of a beam by using a transducer-array to focus the beam in a lateral direction has a convolution relationship with a function defining a shape of the beam in a depth direction through a matched filter. Thus, for each scan line, a signal received in a depth direction is filtered using a matched filter. As a result, a reflection value may be obtained according to a depth of a subject.

SUMMARY

In one general aspect, there is provided a diagnostic image generating apparatus, including a transmitting unit configured to transmit a modulated transmission signal to a subject, a reception beamforming unit configured to form a reception beam by beamforming echo signals reflected from the subject, a point spread function (PSF) estimating unit configured to estimate a PSF for each region according to the formed reception beam, a filtering unit configured to filter the formed reception beam according to the estimated PSF, and a diagnostic image generating unit configured to generate a diagnostic image according to the filtered reception beam.

The general aspect of the apparatus may further provide that the PSF estimating unit is further configured to estimate the PSF according to the formed reception beam in consideration of a depth direction, a lateral direction, or a combination thereof.

The general aspect of the apparatus may further provide that the PSF estimating unit is further configured to estimate the PSF according to an increase or a reduction in a depth in the depth direction.

The general aspect of the apparatus may further provide that the PSF estimating unit is further configured to estimate the PSF according to a change in location in the lateral direction.

The general aspect of the apparatus may further provide that the PSF estimating unit is further configured to estimate a filter according to the estimated PSF, and the filtering unit is further configured to filter the formed reception beam according to the estimated filter.

The general aspect of the apparatus may further provide a demodulating unit configured to demodulate the formed reception beam.

The general aspect of the apparatus may further provide that the PSF estimating unit is further configured to estimate the PSF for each region of the data image according to the demodulated reception beam, and the filtering unit is further configured to filter the demodulated reception beam according to the estimated PSF.

The general aspect of the apparatus may further provide that the modulated transmission signal is a wideband transmission signal.

The general aspect of the apparatus may further provide that the filtering unit is further configured to estimate reflectivity indicating the subject that minimizes a cost value according to the estimated PSF and the formed reception beam, and the diagnostic image generating unit is further configured to generate the diagnostic image according to the estimated reflectivity indicating the subject.

In another general aspect, there is provided a medical image system, including a diagnostic image generating apparatus configured to transmit a modulated transmission signal to a subject, form a reception beam by beamforming echo signals reflected from the subject, estimate a PSF for each region according to the formed reception beam, filter the formed reception beam according to the estimated PSF, and generate a diagnostic image according to the filtered reception beam, and a display unit configured to display the generated diagnostic image.

The general aspect of the system may further provide that the diagnostic image generating apparatus is further configured to estimate the PSF in consideration of a depth direction, a lateral direction, or a combination thereof according to the formed reception beam.

In yet another general aspect, there is provided a beamforming method, including modulating a transmission signal, transmitting the modulated transmission signal to a subject, forming a reception beam by beamforming echo signals reflected from the subject, estimate a PSF for each region according to the formed reception beam, and filtering the formed reception beam according to the estimated PSF.

The general aspect of the method may further provide that the estimating of the PSF includes estimating the PSF according to the formed reception beam in consideration of a depth direction, a lateral direction, or a combination thereof.

The general aspect of the method may further provide that the estimating of the PSF includes estimating the PSF according to an increase or a reduction in a depth in the depth direction.

The general aspect of the method may further provide that the estimating of the PSF includes estimating the PSF according to a change in location in the lateral direction.

The general aspect of the method may further provide estimating a filter according to the estimated PSF, and filtering the formed reception beam according to the estimated filter.

The general aspect of the method may further provide that the modulated transmission signal is a wideband transmission signal.

The general aspect of the method may further provide generating a diagnostic image according to the filtered reception beam, and displaying the generated diagnostic image.

The general aspect of the method may further provide demodulating the formed reception beam. The estimating of the PSF includes estimating the PSF for each region of the data image according to the demodulated reception beam, and the filtering of the formed reception beam includes filtering the demodulated reception beam according to the estimated PSF.

In still another general aspect, there is provided a non-transitory computer readable recording medium having recorded thereon a program configured to execute the beamforming method.

Figure 1:
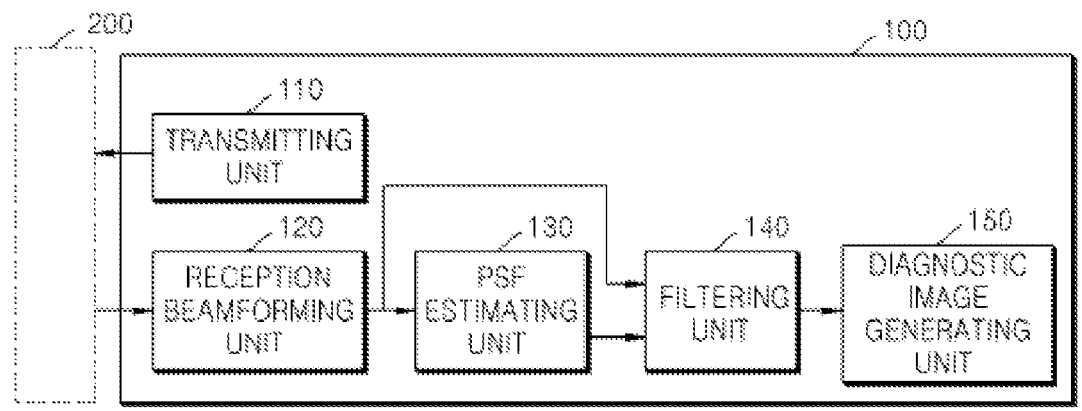
FIG. 1 is a block diagram illustrating an example of a diagnostic image generating apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 is a block diagram illustrating an example of a diagnostic image generating apparatus 100. Referring to FIG. 1, the diagnostic image generating apparatus 100 includes a transmitting unit 110, a reception beamforming unit 120, a point spread function (PSF) estimating unit 130, a filtering unit 140, and a diagnostic image generating unit 150. The diagnostic image generating apparatus 100 may further include general-purpose elements other than those illustrated in FIG. 1.

The transmitting unit 110, the reception beamforming unit 120, the PSF estimating unit 130, the filtering unit 140, and the diagnostic image generating unit 150 may be one or more processors. The processors may be an array of a plurality of logic gates, a combination of a general-purpose microprocessor and memory storing a program to be executed by the processor, or the like.

The diagnostic image generating apparatus 100 of FIG. 1 generates the diagnostic image of a subject. The subject may be a portion of a human being, such as, but not limited to, a breast, a liver, an abdomen, or the like. The diagnostic image may be an ultrasonic image or the like.

The transmitting unit 110 transmits a modulated transmission signal to the subject. For example, the transmitting unit 110 controls a transducer-array 200 to transmit an ultrasonic signal that corresponds with the modulated transmission signal to the subject. In this regard, a modulation unit (illustrated in FIG. 2) modulates the transmission signal. The modulation unit will be described with reference to FIG. 2.

The modulated transmission signal is a wideband transmission signal. In this regard, the wideband transmission signal may be a transmission signal modulated by using a transmission code or a frequency such as, for example, a chirp code, a golay code, or a pseudo-noise (PN) sequence code.

Accordingly, the transmitting unit 110 transmits the modulated transmission signal to the subject using the transducer-array 200, and the reception beamforming unit 120 receives echo signals reflected from the subject using the transducer-array 200. The reception beamforming unit 120 performs reception beamforming on the received echo signals and forms a reception beam. In this regard, the reception beam formed by the reception beamforming unit 120 may be radio frequency (RF) data, but is not limited thereto.

The reception beamforming unit 120 may perform delay and sum (DAS) beamforming on the received echo signals. The DAS beamforming may synthesize the received echo signals by applying a time delay value according to a distance between a focusing point of the subject and the transducer-array 200 that transmits the modulated transmission signal to a beam focusing location of the subject.

The received echo signals are signals obtained by reflecting the modulated transmission signal from the subject. For example, the transmitting unit 110 transmits the wideband transmission signal to the subject through the transducer-array 200. The transducer-array 200 receives echo signals reflected from the subject because of the transmitted wideband transmission signal to the subject. The reception beamforming unit 120 performs reception beamforming on the received echo signals.

The PSF estimating unit 130 estimates a PSF for each region using the reception beam formed by the reception beamforming unit 120. In this regard, the region is a depth direction, a lateral direction, an elevation direction, or any combination thereof. In addition, each region indicates each region of a data image regarding the subject.

For example, the PSF estimating unit 130 estimates the PSF in consideration of the depth direction, the lateral direction, the elevation direction, or any combination thereof. In this regard, estimating the PSF in consideration of the depth direction may include estimating the PSF by increasing or reducing a depth in the depth direction. Further, estimating the PSF in consideration of the lateral direction may include estimating the PSF by changing a location in the lateral direction. Moreover, estimating the PSF in consideration of the elevation direction may include estimating the PSF according to a change in the elevation direction. Accordingly, the PSF estimating unit 130 may estimate one PSF in consideration of the depth direction, the lateral direction, the elevation direction, or any combination thereof, thereby serving to estimate the PSF having a high correlation in the depth and lateral directions.

For example, estimating the PSF for each region may correspond to estimating a PSF with regard to a predetermined region of a RF data image instead of a scanline of the RF data image. In this regard, the predetermined region is defined by two or more of the depth direction, the lateral direction, and the elevation direction.

Thus, the PSF estimating unit 130 may estimate the PSF by increasing or reducing a depth of a focal point in the depth direction (i.e, changing a location of the focal point in the depth direction), changing a location of the focal point in the lateral direction, changing a location of the focal point in the elevation point, or any combination thereof.

Figure 2:
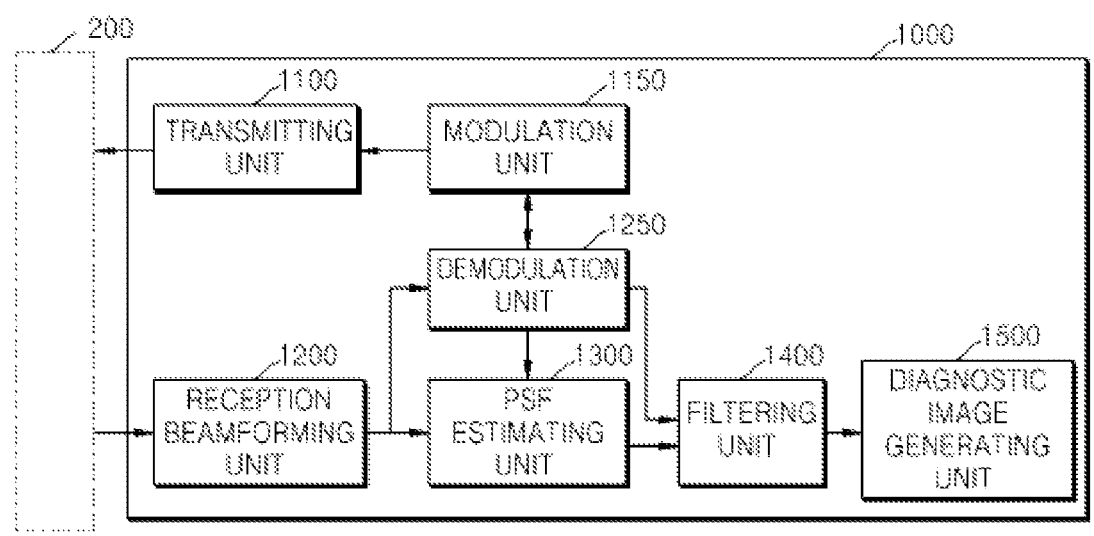
FIG. 2 is a block diagram illustrating another example of a diagnostic image generating apparatus.

The PSF estimating unit 130 may estimate the PSF for each region by using a reception beam that has been demodulated by a demodulation unit (illustrated in FIG. 2). For example, the demodulation unit may perform the demodulation by using a transmission signal with respect to beamformed RF data. In this regard, demodulation may be a filtering operation using a matched filter.

Further, the PSF estimating unit 130 may estimate the PSF using a parametric method or a nonparametric method. Regarding the parametric method, the PSF estimating unit 130 estimates a magnitude and a phase of the PSF by using a reception beam in a frequency domain. In this regard, the PSF estimating unit 130 may estimate a filter while estimating the phase of the PSF. The PSF estimating unit 130 may use a curve fitting method when estimating the magnitude of the PSF, the phase of the PSF, and the filter. That is, the PSF estimating unit 130 may model data to be estimated, and estimate a curve parameter using the curve fitting method. The filter estimated by the PSF estimating unit 130 may be a spatial filter. For example, the filter may include a 2D or 3D window based matched filter, an inverse filter, or a winner filter.

Since the PSF exhibits the characteristics of the diagnostic image generating apparatus 100, the PSF may be included in a baseband spectrum of the reception beam. Thus, the PSF estimating unit 130 may estimate the magnitude of the PSF by performing filtering on the reception beam. That is, the PSF estimating unit 130 may estimate the magnitude of the PSF by performing discrete Fourier transform (DFT) processing on the reception beam, and performing white noise filtering on the reception beam on which the DFT is performed.

The PSF estimating unit 130 may also estimate the phase of the PSF and the filter in a direction of a minimum amplitude multiplication of the estimated magnitude of the PSF and a filtering resultant value. In this regard, the PSF estimating unit 130 may use a maximum a posteriori (MAP) estimation method to estimate the phase of the PSF and the filter.

Regarding the nonparametric method, the PSF estimating unit 130 may estimate the PSF by calculating all data of the PSF for each frequency band or calculating all data values of the PSF in the spatial domain. For example, the PSF estimating unit 130 may estimate the PSF satisfying Equation 1, $$H = \min(HX - Y)^2, \quad \text{[Equation 1]}$$

where H denotes the PSF, X denotes an initial value of reflectivity of the subject or a previously calculated value, and Y denotes the RF data beamformed by using the echo signals reflected from the subject.

The reflectivity of the subject may be data corresponding to the diagnostic image of the subject. The RF data Y reflected from the subject may be the reception beam formed by the reception beamforming unit 120. H, X, and Y may indicate signals converted into a frequency domain by performing Fourier transform (FT) or DFT processing.

Referring to Equation 1, the PSF estimating unit 130 estimates the PSF using the initial value X of reflectivity of the subject. That is, the PSF estimating unit 130 may estimate a PSF having a minimum error between a multiplication of the PSF H and the initial value X of reflectivity of the subject, and the RF data Y reflected from the subject. In this regard, if the initial value X of reflectivity of the subject is not exact, the PSF estimating unit 130 estimates the reflectivity X of the subject again by using the PSF H.

In addition, the PSF estimating unit 130 may estimate the PSF satisfying Equation 2, $$H_s = \min\{(H_s * X_s - Y_s)^2 + a|X_s|\}, \quad \text{[Equation 2]}$$

where $H_s$ denotes the PSF in the spatial domain, $X_s$ denotes an initial value of reflectivity of the subject or a previously calculated value in the spatial domain, $Y_s$ denotes the RF data beamformed by using the echo signals reflected from the subject in the spatial domain, and a denotes a constant parameter.

Referring to Equation 2, the PSF estimating unit 130 may not convert H, X, and Y into the frequency domain but may estimate $H_s$ using a repetitive estimation method by using spatial domain parameters $H_s$, $X_s$, and $Y_s$ of H, X, and Y, respectively.

The filtering unit 140 filters the formed reception beam using the PSF estimated by the PSF estimating unit 130. In this regard, the filtering unit 140 may use the PSF, the filter estimated by the PSF estimating unit 130, or a combination thereof to perform the filtering. The filtering unit 140 may also filter the demodulated reception beam using the PSF when the demodulated reception beam is demodulated by the demodulation unit (illustrated in FIG. 2).

In addition, the filtering unit 140 may deconvolute the PSF estimated by the PSF estimating unit 130 and the reception beam formed by the reception beamforming unit 120 to perform the filtering. For example, since the PSF may exhibit system characteristics of the diagnostic image generating apparatus 100, the echo signals reflected from the subject may be exhibited by convolution of the reflectivity of the subject and the PSF. Thus, the filtering unit 140 may deconvolute the PSF estimated by the PSF estimating unit 130 and the RF data that is beamformed by the reception beamforming unit 120 to perform the filtering.

As another example, the filtering unit 140 may use an inverse filter estimated by the PSF estimating unit 130 to perform the filtering operation on the reception beam formed by the reception beamforming unit 120. Blind convolution may be implemented to perform the estimation of the PSF, the estimation of the filter, and the filtering using the PSF, the filter estimated by the PSF estimating unit 130, or a combination thereof.

In addition, the filtering unit 140 may estimate a reflectivity indicating the subject that minimizes a cost value by using the PSF and the reception beam. For example, the filtering unit 140 may estimate the reflectivity of the subject according to Equation 3, $$X_s = \min\{(H_s * X_s - Y_s)^2 + b|X_s|\}. \quad \text{[Equation 3]}$$

Referring to Equation 3, the filtering unit 140 may calculate X that minimizes the cost value, i.e. the reflectivity indicating the subject, according to a cost function shown in Equation 3 by using the PSF $H_s$ and the RF data $Y_s$ through a matrix operation. In this case, the filtering unit 140 performs filtering according to a complex iteration process rather than a simple filtering operation. In Equation 3, b is a constant parameter.

The diagnostic image generating unit 150 generates the diagnostic image by using the reception beam filtered by the filtering unit 140. The diagnostic image generating unit 150 generates the diagnostic image by using the reflectivity of the subject estimated by the filtering unit 140. For example, the diagnostic image generating unit 150 includes a digital signal processor (DSP) (not shown) and a digital scan converter (DSC) (not shown), or the like. The DSP processes a signal output by the filtering unit 140 and forms image data presenting a b-mode (brightness-mode), a c-mode (color-mode), or a d-mode (doppler-mode). The DSC generates a scan-converted diagnostic image to display the image data formed by the DSP.

FIG. 2 is a block diagram illustrating an example of a diagnostic image generating apparatus 1000. Referring to FIG. 2, the diagnostic image generating apparatus 1000 includes a transmitting unit 1100, a modulation unit 1150, a reception beamforming unit 1200, a demodulation unit 1250, the PSF estimating unit 1300, a filtering unit 1400, and a diagnostic image generating unit 1500. The diagnostic image generating apparatus 1000 may further include general-purpose elements other than those illustrated in FIG. 2.

The transmitting unit 1100, the modulation unit 1150, the reception beamforming unit 1200, the demodulation unit 1250, the PSF estimating unit 1300, the filtering unit 1400, and the diagnostic image generating unit 1500 may be one or more processors.

The diagnostic image generating apparatus 1000 of FIG. 2 is another example of the diagnostic image generating apparatus 100 of FIG. 1, and is thus not limited to the elements illustrated in FIG. 2. The above descriptions related to the transmitting unit 110, the reception beamforming unit 120, the PSF estimating unit 130, the filtering unit 140, and the diagnostic image generating unit 150 of FIG. 1 are applied to the diagnostic image generating apparatus 1000 of FIG. 2 and will not be described again here.

The diagnostic image generating apparatus 1000 generates a diagnostic image of a subject. In this regard, the subject may be a portion of a human being, such as, but not limited to, a breast, a liver, an abdomen, or the like. The diagnostic image may be an ultrasonic image or the like.

The modulation unit 1150 modulates a transmission signal. For example, the modulation unit 1150 modulates the transmission signal by using a transmission code or a frequency. Thus, the modulated transmission signal may be a wideband transmission signal. For example, the modulation unit 1150 may modulate the transmission signal by using, for example, a chirp code, a golay code, a PN sequence code, or the like.

The transmitting unit 1100 transmits the modulated transmission signal to the subject. The reception beamforming unit 1200 performs reception beamforming on echo signals reflected from the subject and forms a reception beam.

The demodulation unit 1250 demodulates the reception beam formed by the reception beamforming unit 1200. For example, the demodulation unit 1250 may demodulate the reception beam formed by the reception beamforming unit 1200 according to a demodulation code or a demodulation frequency of a demodulated transmission signal. Regarding the demodulating performed according to the demodulation code, for example, the demodulation unit 1250 demodulates the reception beam formed by the reception beamforming unit 1200 by using a signal corresponding to the demodulation code or the like. Regarding the demodulating performed according to the demodulation frequency, for example, the demodulation unit 1250 may include a low pass filter (LPF) and a transmission signal based matched filter, a cosine multiplier, a sine multiplier, or any combination thereof, but is not limited thereto.

The PSF estimating unit 1300 estimates a PSF for each region by using the reception beam formed by the reception beamforming unit 1200. However, the PSF estimating unit 1300 may estimate the PSF for each region by using the demodulated reception beam demodulated by the demodulation unit 1250.

The filtering unit 1400 performs a filtering operation on the demodulated reception beam demodulated by the demodulation unit 1250 by using the PSF estimated by the PSF estimating unit 1300. The diagnostic image generating unit 1500 generates the diagnostic image by using the reception beam filtered by the filtering unit 1400.

Figure 3:
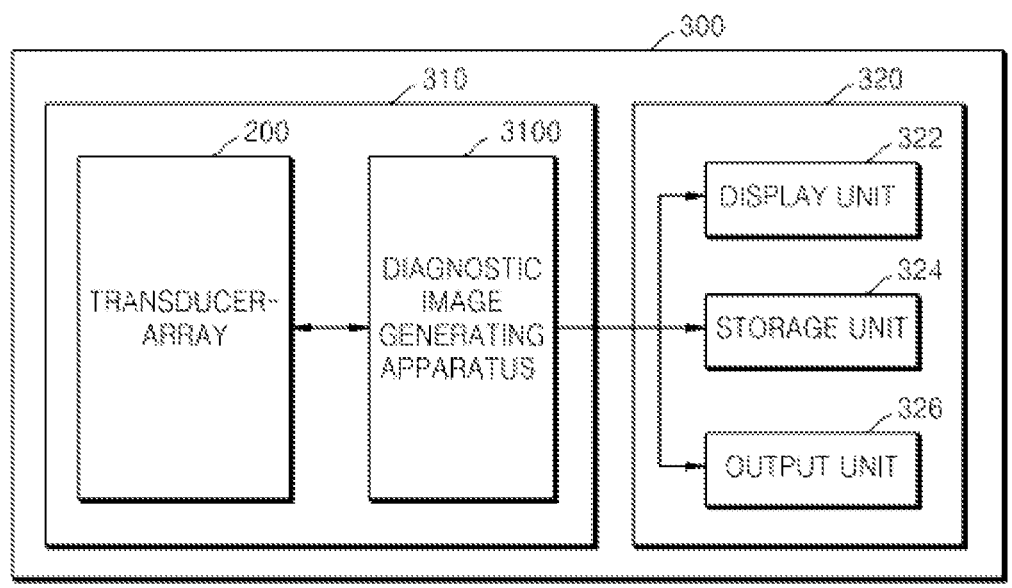
FIG. 3 is a block diagram illustrating an example of a medical image system.

FIG. 3 is a block diagram illustrating an example of a medical image system 300. Referring to FIG. 3, the medical image system 300 includes a probe 310 and a main body 320. The probe 310 includes the diagnostic image generating apparatus 3100 and the transducer-array 200. The main body 320 includes a display unit 322, a storage unit 324, and an output unit 326. The medical imaging system 300 may further include general-purpose elements other than the elements illustrated in FIG. 3.

The diagnostic image generating apparatus 3100 and the transducer-array 200 illustrated in FIG. 3 are other respective examples of the diagnostic image generating apparatus 100 and the diagnostic image generating apparatus 1000 respectively illustrated in FIGS. 1 and 2, and the transducer-array 200 illustrated in FIGS. 1 and 2. Thus, the descriptions related to FIGS. 1 and 2 are applied to the medical imaging system 300 of FIG. 3 and will be omitted here.

The medical imaging system 300 provides a diagnostic image of a subject. For example, the medical imaging system 300 displays a diagnostic image of a subject or outputs a signal representing the diagnostic image of the subject to an external device capable of displaying the diagnostic image.

The probe 310 transmits a transmission signal to the subject, receives echo signals reflected from the subject, and generates the diagnostic image of the subject by using the received echo signals. The transducer-array 200 includes one or more transducers. Each of the transducers included in the transducer-array 200 converts an electrical signal into an ultrasonic signal, transmits the ultrasonic signal to the subject, reconverts the ultrasonic signal reflected from the subject into the electrical signal, and transfers the electrical signal to the diagnostic image generating apparatus 3100.

The diagnostic image generating apparatus 3100 transmits a modulated transmission signal to the subject through the transducer-array 200, forms a reception beam by performing reception beamforming on the echo signals reflected from the subject, estimates a PSF for each region using the formed reception beam, filters the reception beam by using the estimated PSF beam, and generates the diagnostic image by using the filtered reception beam.

The probe 310 generates the diagnostic image, but is not limited thereto. The probe 310 performs the filtering and the main body 320 generates the diagnostic image using a filtered reception beam.

The main body 320 drives the medical image system 300 and displays, stores, and outputs the diagnostic image of the subject. The display unit 322 displays the diagnostic image generated by the diagnostic image generating apparatus 3100. For example, the display unit 322 includes various output devices, such as a display panel, a liquid crystal display (LCD) screen, a monitor, and the like included in the medical imaging system 300. The medical imaging system 300 may not include the display unit 322 and, instead, include the output unit 326 to output the diagnostic image generated by the diagnostic image generating apparatus 3100 to an external display device (not shown).

The storage unit 324 stores data generated during an operation of the medical imaging system 300. For example, the storage unit 324 may store the reception beam formed by the diagnostic image generating apparatus 3100, image data representing a, b, c, or d mode, scan-converted diagnostic images, or the like. The storage unit 324 is a general storage medium. As such, the storage unit 324 may include a hard disc drive (HDD), read only memory (ROM), random access memory (RAM), flash memory, and a memory card, but is not limited thereto.

The output unit 326 exchanges data with an external device via a wired/wireless network or wired serial communication. In this case, the wired/wireless network may include the Internet, a local area network (LAN), a wireless LAN, a wide area network (WAN), a personal area network (PAN), or the like, but is not limited thereto and may be a different type of a network via which information is exchanged. The storage unit 324 and the output unit 326 may be a single body, and may include other operations, such as image interpretation and image searching to form a picture archiving communication system (PACS).

Figure 4:
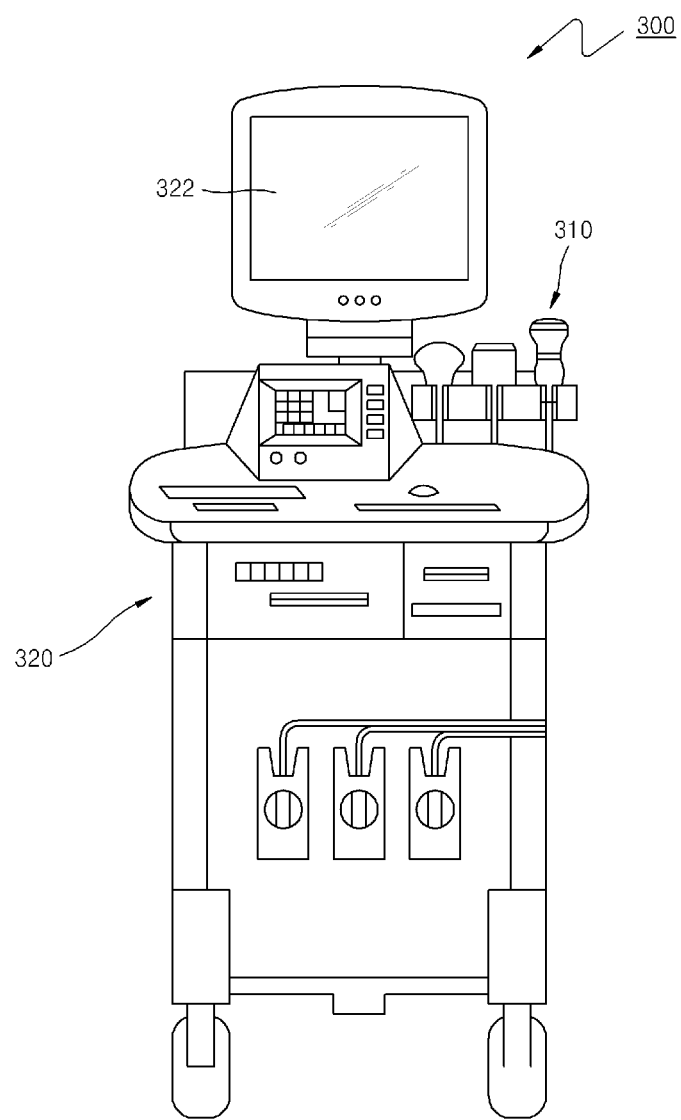
FIG. 4 is a diagram illustrating another example of a medical image system.

FIG. 4 is a diagram illustrating an example of the medical image system 300. The medical image system 300 of FIG. 4 is a plan illustration of the medical image system 300 of FIG. 3. Thus, the above descriptions related to FIG. 3 may also be applied to the medical image system 300 of FIG. 4 and will not be described again here.

As shown in FIG. 4, the medical image system 300 includes the probe 310 that transmits and receives a signal to and from a subject and performs beamforming by using the received signal, and the main body 320 that processes data obtained from the probe 310 and displays, stores, and outputs the data. In this regard, the main body 320 may further include the display unit 322 that displays a diagnostic image generated by the probe 310. The main body 320 may further include the storage unit 324 and the output unit 326 therein, and, in place of the probe 310, may generate the diagnostic image.

Figure 5:
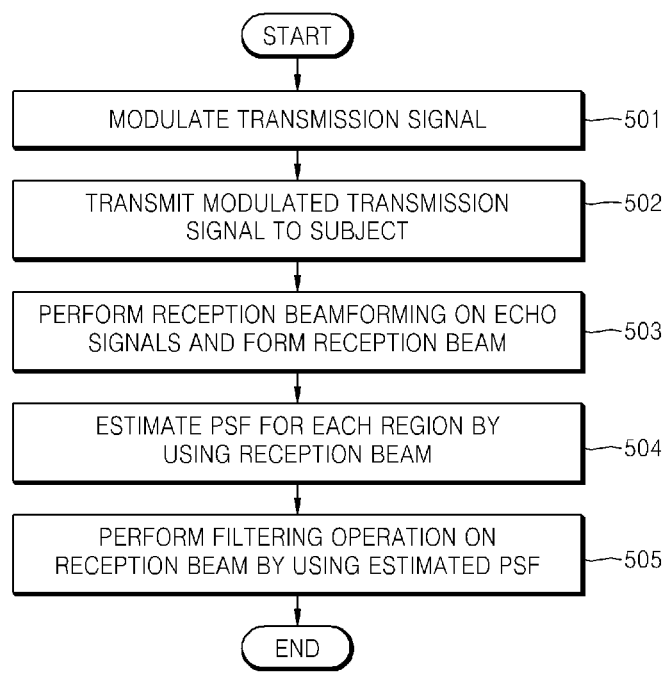
FIG. 5 is a flowchart illustrating an example of a beamforming method.

FIG. 5 is a flowchart illustrating an example of a beamforming method. Referring to FIG. 5, the beamforming method may be performed by the diagnostic image generating apparatuses 100, 1000, and 3100, the transducer-array 200, or the medical image system 300 illustrated in FIGS. 1-4. Thus, although not described here, the above descriptions related to the diagnostic image generating apparatuses 100, 1000, and 3100, the transducer-array 200, or the medical image system 300 illustrated in FIGS. 1-4 may also be applied to the beamforming method of FIG. 5.

The beamforming method may be performed by using one or more processors. Further, although the beamforming method described relates to an ultrasonic image, it is not limited thereto. As such, various ultrasonic image technologies, such as an elastic image and radar and sound signal processing, may be applied to the beamforming method.

A transmission signal is modulated (501). For example, the modulation unit 1150 of FIG. 2 may modulate the transmission signal using a frequency or a code sequence.

The modulated transmission signal is transmitted (502) to a subject. In this regard, the modulated transmission signal may be a wideband transmission signal, but is not limited thereto.

Reception beamforming is performed (503) on an echo signal of the transmitted modulated transmission signal reflected from the subject. Subsequently, a reception beam is formed. For example, the reception beamforming unit 120 and 1200 may perform DAS beamforming on the echo signal of the transmitted modulated transmission signal reflected from the subject, but is not limited thereto.

A PSF is estimated (504) for each region using the formed reception beam. In this regard, the PSF estimating unit 130 and 1300 may estimate the PSF in consideration of a depth direction, a lateral direction, or a combination thereof. For example, the PSF estimating unit 130 may estimate the PSF by increasing or reducing a depth in the depth direction or changing a location in the lateral direction.

The formed reception beam is filtered (505) using the estimated PSF.

According to teachings above, there is provided a diagnostic image generating apparatus having a reception beamforming unit that performs reception beamforming on the echo signals reflected from the subject as the wideband transmission signal is transmitted, which may enhance a transmission/reception speed between the subject and the diagnostic image generating apparatus, a signal to noise ratio (SNR) of a high spatial frequency, and a resolution of the diagnostic image generated by the diagnostic image generating apparatus.

According to teachings above, there is provided a diagnostic image generating apparatus having a PSF estimating unit estimating a PSF for each region by using the reception beam formed by the reception beamforming unit, which may provide enhanced resolution and SNR in the lateral and elevation directions as well as the depth direction in the diagnostic image generated by the diagnostic image generating apparatus.

According to teachings above, there is provided a diagnostic image generating apparatus, a medical image system, and a beamforming method that may enhance an SNR and a resolution of the diagnostic image indicating the subject in the lateral direction and an elevation direction besides the depth direction.

According to teachings above, there is provided a diagnostic image generating apparatus that may enable the generation of a diagnostic image having a high resolution.

The units described herein may be implemented using hardware components and software components, such as, for example, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data that can be thereafter read by a computer system or processing device. Examples of the computer readable recording medium include read-only memory (ROM), random-access memory (RAM), CD-ROMs, magnetic tapes, floppy disks, optical data storage devices. In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. In addition, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A beamforming method, comprising:
   modulating a transmission signal;
   transmitting the modulated transmission signal to a subject;
   forming a reception beam by beamforming echo signals reflected from the subject;
   estimating a point spread function (PSF) for each region of a data image by applying the formed reception beam;
   estimating a filter using the estimated PSF; and
   filtering the formed reception beam by application of the estimated PSF and the estimated filter, wherein the estimating of the PSF comprises estimating the PSF by application of the formed reception beam in a depth direction corresponding to a z direction of an xyz cartesian coordinate system, a lateral direction corresponding to an x direction of the xyz cartesian coordinate system, and an elevation direction corresponding to a y direction of the xyz cartesian coordinate system,
   wherein the filter comprises a spatial filter.

2. The method of claim 1, wherein the estimating of the PSF comprises estimating the PSF by application of an increase or a reduction in a depth in the depth direction.

3. The method of claim 1, wherein the estimating of the PSF comprises estimating the PSF by application of a change in location in the lateral direction.

4. The method of claim 1, wherein the modulated transmission signal is a wideband transmission signal.

5. The method of claim 1, further comprising:
   generating a diagnostic image by application of the filtered reception beam; and
   displaying the generated diagnostic image.

6. The method of claim 1, further comprising:
   demodulating the formed reception beam,
   wherein the estimating of the PSF comprises estimating the PSF for each region of the data image by application of the demodulated reception beam, and
   wherein the filtering of the formed reception beam comprises filtering the demodulated reception beam by application of the estimated PSF.

7. A non-transitory computer readable recording medium having recorded thereon a program configured to execute the method of claim 1.

* * * * *